United States Patent [19]

Cooper

[11] Patent Number: 4,969,456
[45] Date of Patent: Nov. 13, 1990

[54] APPARATUS FOR USE IN APPLYING MOUTH TO MOUTH RESUSCITATION

[75] Inventor: Johnny R. Cooper, Arlington, Tex.

[73] Assignee: Tri Jon, Inc., Independence, Oreg.

[21] Appl. No.: 100,484

[22] Filed: Sep. 24, 1987

[51] Int. Cl.⁵ ............................................. A61M 16/00
[52] U.S. Cl. ............................ 128/203.11; 128/205.21
[58] Field of Search ........................ 128/202.28, 202.29, 128/203.11, 205.24, 206.15, 207.12; 132/511, 516.11, 516.15, 517, 519; 251/338

[56] References Cited

U.S. PATENT DOCUMENTS

| 417,795 | 12/1889 | Starr | 128/205.29 |
| 913,688 | 3/1909 | Bucklen | 128/207.16 |
| 1,848,234 | 3/1932 | Swope et al. | 128/205.24 |
| 2,280,050 | 4/1942 | Alexander et al. | 128/203.11 |
| 2,640,481 | 6/1953 | Conley | 128/206.15 |
| 3,099,985 | 8/1963 | Wilson et al. | 128/203.11 |
| 3,137,293 | 6/1964 | Green | 128/29 |
| 3,252,457 | 5/1966 | Monaca et al. | 128/203.11 |
| 3,346,011 | 10/1962 | Johannisson | 128/205.24 |
| 3,802,428 | 4/1974 | Sherman | 128/145.5 |
| 3,957,046 | 5/1976 | Harris | 128/203.11 |
| 4,106,502 | 8/1978 | Wilson | 128/203.11 |
| 4,223,789 | 9/1980 | Mahoney | 128/206.24 |
| 4,360,017 | 11/1982 | Barlett | 128/202.28 |
| 4,538,607 | 9/1988 | Saul | 128/207.16 |
| 4,559,940 | 12/1985 | McGinnis | 128/202.26 |
| 4,572,175 | 2/1986 | Flynn | 128/203.11 |

FOREIGN PATENT DOCUMENTS

| 906809 | 8/1972 | Canada | 128/202.28 |
| 2792213 | 3/1979 | Fed. Rep. of Germany | 128/203.1 |
| 901357 | 7/1962 | United Kingdom | 128/202.28 |

Primary Examiner—Max Hindenburg
Assistant Examiner—K. M. Reichle

[57] ABSTRACT

An apparatus for use in applying mouth to mouth resuscitation, having a tube for insertion into a victim's mouth and a circular, convex shield attached to one end of the tube. A one-way valve, within the tube, allows air to flow through the tube only in a direction away from the shield. A wafer mounted within the tube, is moveable between an open position and a closed position. The wafer has a plurality of notches spaced around the perimeter. The wafer is mounted between first and second annular shoulders within the valve. When the wafer is in the closed position, the first annular shoulder blocks airflow through the notches in the wafer. When the wafer is in the open position, the second annular shoulder allows air to flow through the notches. The apparatus also has a screen for preventing solids of a certain size or larger from entering the valve.

17 Claims, 1 Drawing Sheet

APPARATUS FOR USE IN APPLYING MOUTH TO MOUTH RESUSCITATION

BACKGROUND OF THE INVENTION

1. Field of the Invention

This invention relates in general to an apparatus for facilitating the administration of artificial respiration. In particular, the invention relates to disposable resuscitators.

2. Description of the Prior Art

Mouth to mouth resuscitation is a well-known and highly recommended method of artificial respiration. Mouth to mouth resuscitation is also an element of cardiopulmonary resuscitation (CPR). The CPR procedure is designed to restore normal breathing after cardiac arrest. The CPR procedure includes mouth to mouth resuscitation and heart massage by the exertion of pressure on the chest.

There are several problems associated with the application of mouth to mouth resuscitation. The personal contact required by the procedure may be considered unpleasant. More importantly, the victim may suffer from a contagious disease which may be transmitted to the rescuer. Also, the victim, particularly a drowning victim, is likely to regurgitate fluids and other matter.

A variety of resuscitators have been devised for use in applying mouth to mouth resuscitation. Some of these prior art devices comprise a tube for insertion into a victim's mouth and a shield attached to one end of the tube. Some prior art resuscitators have one way valves to prevent the flow of air or other fluids through the tube from the victim to the rescuer.

SUMMARY OF THE INVENTION

The apparatus of the invention includes a tube for insertion into a victim's mouth and a shield attached to one end of the tube. The shield has an aperture aligned with the tube and is concave toward the tube.

A one-way valve within the tube allows air to flow through the tube from the rescuer to the victim. The valve blocks the flow of air and other fluids in the opposite direction. One end of the valve is flush with the surface of the shield.

A wafer is mounted within the valve, and is moveable between an open position and a closed position. The wafer has a plurality of notches evenly spaced around the perimeter of the wafer.

Two annular shoulders are formed within the valve. The open position of the wafer is against one of the shoulders, and the closed position of the wafer is against the other shoulder. The first shoulder blocks airflow through the notches when the wafer is in the closed position. The second annular shoulder allows air to flow through the notches when the wafer is in the open position.

A screen is mounted on one end of the tube. The screen prevents solids of a certain size or larger from entering the valve.

DESCRIPTION OF THE PREFERRED EMBODIMENT

Figure 1:
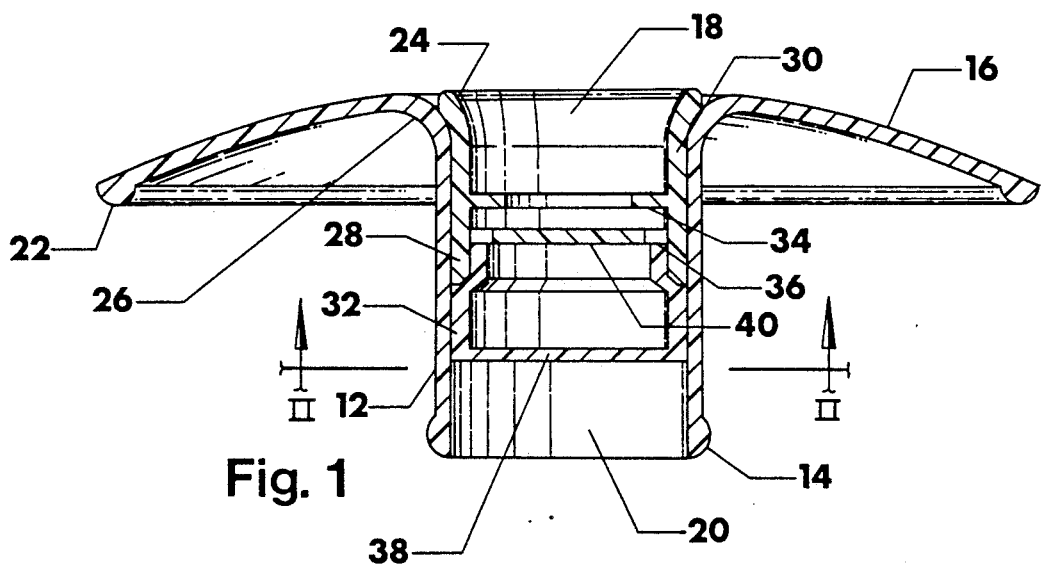
FIG. 1 is a sectional side view of the apparatus of the invention, showing the wafer in the open position.
Figure 2:
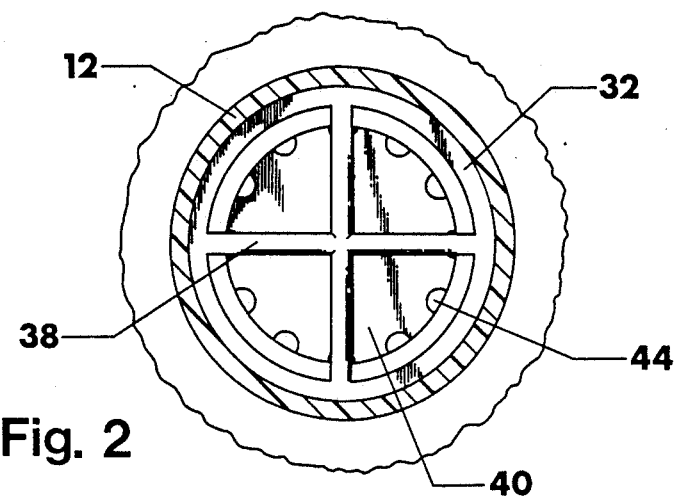
FIG. 2 is a sectional view of the apparatus of the invention, as seen along lines II—II in FIG. 1.
Figure 3:
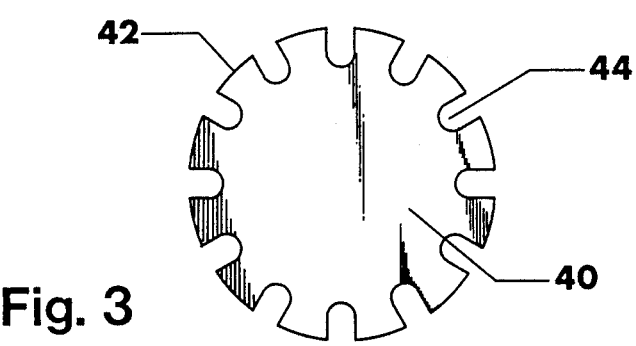
FIG. 3 is a top view of the wafer of the apparatus of the invention.

As shown in FIG. 1, the apparatus of the invention has a tube 12 for insertion into a victim's mouth. The tube has a diameter of approximately one inch, and is approximately one and one-half inches long. A slight enlargement of the outer diameter creates a ridge 14 near one end of the tube 12. This ridge 14 helps to hold the apparatus in the victim's mouth during the resuscitation procedure.

A circular shield 16 is integrally attached to the other end of the tube 12. The shield 16 has an aperture 18, which is aligned with the bore 20 of the tube 12.

The circular shield 16 is concave toward the tube 12. The shield 16 has an enlarged ridge 22 around its outer circumference. The intersection between the aperture 18 of the shield 16 and the end of the tube 12 is rounded on both the inner surface 24 and the outer surface 26. This eliminates any undesirable sharp corners.

The tube 12 and the shield 16 are made of a transparent, soft, latex rubber. This material separates the rescuer from the victim, and adequately protects the rescuer from contact with the victim. The transparency of the material allows visual inspection of the victim at all times.

A one-way valve 28 is located within the tube 12. The one-way valve 28 has an upper section 30 and a lower section 32, which snap together telescopically. The upper section 30 has a first annular shoulder 34, which faces downward. The upper end of the lower section 32 forms an upwardly facing second annular shoulder 36. The lower section 32 also has a screen 38. This screen 38 is designed to keep solids of a certain size or larger from entering the valve 28.

A wafer 40 is mounted within the valve 28 between the first shoulder 34 and the second shoulder 36. The wafer 40 is flat and round, having an outer perimeter 42. Twelve notches 44 are evenly spaced around the perimeter 42 of the wafer 40.

The wafer 40 is moveable between an open position, against the second annular shoulder 36, and a closed position, against the first annular shoulder 34. When the wafer 40 is in the open position, as shown in FIG. 1, the second annular shoulder 36 allows air to pass through the notches 44. When the wafer 40 is the closed position, the first annular shoulder 34 blocks the flow of air and other fluids through the notches 44.

In operation, the tube 12 is inserted into the mouth of the victim. The convex shield 16 thus covers the lower portion of the victim's face. The rescuer can then blow into the upper end of the tube 12 through the aperture 18 in the shield 16. When the rescuer blows into the tube 12, the wafer 40 moves to the open position, shown in FIG. 1. Air flows through the bore 20, through the notches 44, and through the one way valve 28.

If the victim exhales or regurgitates, the wafer 40 moves to the closed position against the first annular shoulder 34. The first shoulder 34 blocks airflow through the notches 44. Between breaths, the rescuer can raise his head away from the tube 12. This relieves the seal of the shield 16 against the face of the victim. The victim can then exhale, but the one-way valve 28 keeps air and other fluids from passing through the tube 12. The shield 16 also keeps the victim's breath and other fluids away from the rescuer.

The apparatus of the invention has several advantages over the prior art. The apparatus of the invention gives the rescuer limited protection from contagious diseases that the victim may have. The apparatus is inexpensive to make and easy to use. The one-way valve 28 is inexpensive and reliable.

The apparatus of the invention has been shown only in the preferred embodiment. It should be apparent that various modifications may be made to the apparatus without departing from the scope of the invention.

I Claim:

1. An apparatus for use in applying mouth to mouth resuscitation to a victim, the apparatus comprising:
   a tube having a first end adapted for fluid communication with a rescuer's mouth and a second end adapted for insertion into the victim's mouth;
   a shield, attached to the first end of the tube, having an aperture aligned with the tube; and
   a one-way valve mounted in the tube having first and second spaced annular shoulders, the first should being adjacent the first end of the tube, and the second shoulder being adjacent the second end of the tube, the radial dimension of the first shoulder being greater than the radial dimension of the second shoulder, and a wafer mounted between the two shoulders for movement between a closed position against the first shoulder and an open position against the second shoulder, and wherein the wafer has a perimeter and a plurality of notches in the perimeter, the radial dimensions of the notches being smaller than the first shoulder and larger than the second shoulder, whereby the first shoulder blocks the flow of air and other fluids through the notches when the wafer in the closed position and the second shoulder allows air and other fluids to flow through the notches when the wafer is in the closed position.

2. The apparatus, as recited in claim 1, wherein the shield is circular.

3. The apparatus, as recited in claim 2, wherein the shield is concave toward the tube.

4. The apparatus, as recited in claim 3, wherein one end of the valve is flush with the first end of the tube.

5. The apparatus, as recited in claim 3, further comprising a screen mounted across the second end of the tube for preventing solids of a certain size or larger from entering the valve.

6. The apparatus, as recited in claim 2, wherein one end of the valve is flush with the first end of the tube.

7. The apparatus, as recited in claim 6, further comprising a screen mounted across the second end of the tube for preventing solids of a certain size or larger from entering the valve.

8. The apparatus, as recited in claim 2, further comprising a screen mounted across the second end of the tube for preventing solids of a certain size or larger from entering the valve.

9. The apparatus, as recited in claim 1, wherein the shield is concave toward the tube.

10. The apparatus, as recited in claim 9, wherein one end of the valve is flush with the first end of the tube.

11. The apparatus, as recited in claim 10, further comprising a screen mounted across the second end of the tube for preventing solids of a certain size or larger from entering the valve.

12. The apparatus, as recited in claim 9, further comprising a screen mounted across the second end of the tube for preventing solids of a certain size or larger from entering the valve.

13. The apparatus, as recited in claim 1, wherein one end of the valve is flush with the first end of the tube.

14. The apparatus, as recited in claim 13, further comprising a screen mounted across the second end of the tube for preventing solids of a certain size or larger from entering the valve.

15. The apparatus, as recited in claim 1, further comprising a screen mounted across the second end of the tube for preventing solids of a certain size or larger from entering the valve.

16. An apparatus for use in applying mouth to mouth resuscitation to a victim, the apparatus comprising:
    a tube having a first end adapted for fluid communication with a rescuer's mouth and a second end adapted for insertion into the victim's mouth;
    a circular shield, attached to the first end of the tube, having an aperture aligned with the tube, and being concave toward the tube;
    a one-way valve mounted in the tube, having one end of the valve flush with the first end of the tube, and having first and second spaced annular shoulders, the first shoulder being adjacent the first end of the tube and the second shoulder being adjacent the second end of the tube, the radial dimension of the first shoulder being greater than the radial dimension of the second shoulder, and a wafer mounted between the two shoulders for movement between a closed position against the first shoulder and an open position against the second shoulder, and wherein the wafer has a perimeter and a plurality of notches in the perimeter, the radial dimensions of the notches being smaller than the first shoulder and larger than the second shoulder, whereby the first annular shoulder blocks the flow of air and other fluids through the notches when the wafer is in the closed position and the second annular shoulder allows airflow through the notches when the wafer is in the open position; and
    a screen mounted across the second end of the tube for preventing solids of a certain size or larger from entering the 17. An apparatus for use in applying mouth to mouth resuscitation to a victim, the apparatus comprising:
    a tube having a first end adapted for fluid communication with a rescuer's mouth and a second end adapted for insertion into the victim's mouth;
    a shield, attached to the first end of the tube, having an aperture aligned with the tube; and
    a one-way valve mounted in the tube having first and second spaced annular shoulders, the first shoulder being adjacent the first end of the tube and the second shoulder being adjacent the second end of the tube, the radial dimension of the first shoulder being greater than the radial dimension of the second shoulder, and a wafer having a perimeter mounted between the two shoulders for movement between a closed position, wherein the perimeter of the wafer engages the first shoulder, and an open position, wherein the perimeter of the wafer engages the second shoulder, and wherein the wafer has a plurality of notches in the perimeter, the radial dimensions of the notches being smaller than the first shoulder and larger than the second shoulder, whereby the first shoulder blocks the flow of air and other fluids through the notches when the wafer is in the closed position and the second shoulder allows air and other fluids to flow through the notches when the wafer is in the closed position.

* * * * *